United States Patent [19]

Schindler et al.

[11] Patent Number: 4,474,691
[45] Date of Patent: Oct. 2, 1984

[54] CHROMOPHORIC PEPTIDES, A PROCESS FOR THEIR PREPARATION, AGENTS CONTAINING THEM AND THEIR USE FOR DETERMINING DD-CARBOXYPEPTIDASES

[75] Inventors: Peter Schindler, Mörfelden-Walldorf; Wolfgang König, Hofheim am Taunus, both of Fed. Rep. of Germany

[73] Assignee: Hoechst Aktiengesellschaft, Frankfurt, Fed. Rep. of Germany

[21] Appl. No.: 480,098

[22] Filed: Mar. 29, 1983

[30] Foreign Application Priority Data

Mar. 31, 1982 [DE] Fed. Rep. of Germany ....... 3211932

[51] Int. Cl.$^3$ ............................................. C07C 103/52
[52] U.S. Cl. ............................................. 260/112.5 R
[58] Field of Search .................................. 260/112.5 R

[56] References Cited

FOREIGN PATENT DOCUMENTS 2497798  7/1982  France ........................ 260/112.5 R

OTHER PUBLICATIONS

Chem. Abstr. vol. 90, (1979) 138198k.
Chem. Abstr. vol. 79, (1973) 115882n.
Chem. Abstr. vol. 99, (1983) 49932p.
Chem. Abstr. vol. 95, (1981) 164921p.

Primary Examiner—Delbert R. Phillips
Attorney, Agent, or Firm—Finnegan, Henderson, Farabow, Garrett & Dunner

[57] ABSTRACT

The invention relates to chromophoric peptides of the general formula I

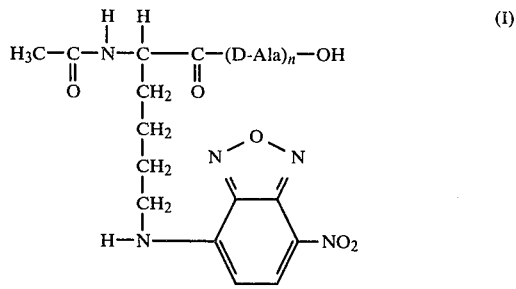

in which n represents 1 or 2, a porcess for their preparation, agents containing them and their use for determining DD-carboxypeptidases.

1 Claim, No Drawings

CHROMOPHORIC PEPTIDES, A PROCESS FOR THEIR PREPARATION, AGENTS CONTAINING THEM AND THEIR USE FOR DETERMINING DD-CARBOXYPEPTIDASES

The invention relates to compounds of the general formula I

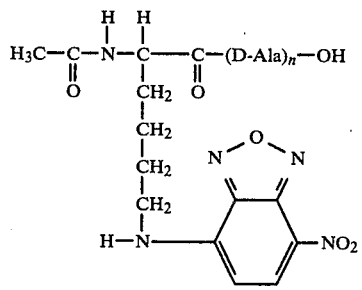

in which n represents 1 or 2.

The quantitative determination of β-lactam antibiotics in biological systems such as, for example, blood, urine, foodstuffs or fermentation broths is of considerable importance. A universally applicable method, with which nanograms of β-lactam per ml can be reliably determined, was recently described by Frère, J.-M. et al. (Antimicrob. Agents Chemother. 1980, 18, 506–510). This method utilizes the property of β-lactam antibiotics of inactivating the enzyme DD-carboxypeptidase from streptomyces R 39 with formation of a stoichiometric complex. After titration of the DD-carboxypeptidase with β-lactams, the remaining enzyme activity is determined. For this purpose, the authors use Nα, Nε-diacetyl-L-lysyl-D-alanyl-D-alanine, the terminal D-alanine of which is cleaved off by DD-carboxypeptidase. The liberated D-alanine is quantitatively determined in a D-aminoacid oxidase/peroxidase/o-dianisidine-coupled test mixture.

Chromophoric substrates offer significant advantages compared to a multiply coupled test mixture of this type, since the substrate and the product from the reaction carrying the chromophore, after separation in a suitable system, preferably using chromatography, are identified by their characteristic inherent color without further measures. Moreover, in principle, interfering effects as are known for the determination of reaction products using coupled test mixtures, do not occur.

It has now been found, surprisingly, that the chromophore-containing tripeptide of the formula I in which n represents 2 is specifically cleaved by the DD-carboxypeptidase from streptomyces R 39 with at least the same efficiency as Nα, Nε-diacetyl-L-lysyl-D-alanyl-D-alanine. Thus the sensitivity of the β-lactam determination reported by Frère et al. can be utilized to the full using the compound according to the invention.

The new chromophore-containing tripeptide has an intense yellow color and is also distinguished by its strong fluorescence in the long-wavelength UV.

DD-carboxypeptidase preparations from streptomyces R 39 cleave off, in a specific manner, the C-terminal D-alanine residue from this tripeptide (also referred to as the "substrate" in the following text), with formation of the dipeptide of the formula I according to the invention with n=1 (also referred to as the "product" in the following text) which carries the chromophore and which can be easily separated from the compound of the formula I (n=2) according to the invention, for example by chromatography on suitable support material.

The invention also relates to a process for the preparation of chromophoric peptides of the general formula I, which comprises reacting Nα-acetyl-N-[4-(7-nitrobenzofurazanyl)]-L-lysine (=Ac-Lys(NBF)-OH) with a compound of the general formula II $$H-(D-Ala)_n-X \qquad (II)$$

in which X denotes OH or OBu$^t$ and n represents 1 or 2, and then, in the case of the tert.-butyl ester, cleaving off the tert.-butyl group preferably with acid.

The condensation of Ac-Lys(NBF)-OH with peptides is particularly crucial, since α-acetylaminoacids tend, on activation of their carboxyl group, to racemize because of the possible formation of an azlactone. Thus, only those methods which show only little racemization may be used for the condensation. In the reaction of Ac-Lys(NBF)-OH with H-D-Ala-D-Ala-OH initially Ac-Lys(NBF)-OH must be preactivated, since the free carboxyl group of H-D-Ala-D-Ala-OH would interfere. For preactivation without racemization of peptides or aminoacid derivatives, which tend to racemize because of their tendency to form azlactones, apart from the azide method, preactivation with dicyclohexylcarbodiimide (DCC) and 3-hydroxy-4-oxo-3,4-dihydro-1,2,3-benzotriazine (HOObt) (Chem. Ber. 103, 2034–2040, 1970) is particularly suitable. For this purpose, in our case, Ac-Lys(NBF)-OH is dissolved with molar amounts of HOObt, preferably in dipolar aprotic solvents, such as, for example, tetrahydrofuran, dimethylformamide, dimethylacetamide or similar, and DCC is added at −10° C. to +10° C., preferably at −2° to +2° C. The reaction is allowed to continue for about 1 to 2 hours and then the amino component H-D-Ala-D-Ala-OH is added, the mixture is stirred until everything has dissolved and is then worked up in a suitable manner.

For the reaction of Ac-Lys(NBF)-OH with H-D-Ala-D-Ala-OBu$^t$, it is also possible to use a simpler procedure, a so-called one-pot method. In this, the carboxyl component and the amino component are dissolved in a suitable solvent and the condensing agent is added. Again, racemization must be taken into account in this case, so that again only methods with a low tendency to produce racemization are suitable. In this instance, because of the simple procedure, the DCC method with the addition of various possible N-hydroxy compounds, such as, for example, 1-hydroxybenzotriazole (HOBt), HOObt or N-hydroxysuccinimide, is suitable. The starting substances necessary for carrying out the process according to the invention are known from the literature or can be prepared by processes known from the literature.

The invention also relates to a procedure for determining DD-carboxypeptidases, which comprises incubating a solution of the compound of the formula I in which n is 2 with the sample for analysis containing the DD-carboxypeptidases, separating off the resulting compound of the formula I in which n is 1, and quantitatively determining the amount of it.

The invention also relates to the use of the chromophoric peptides of the general formula I for determining DD-carboxy peptidase inhibitors and for determining β-lactams after the pre-incubation with DD-carboxypeptidases, and to agents containing peptides of the formula I.

The advantageous procedure for the quantitative determination of the DD-carboxypeptidases is such that suitably buffered aqueous solutions of the tripeptide of the formula I are incubated with DD-carboxypeptidases. For example, a 50 mM tris-HCl buffer of pH 8.3, which contains 0.1 M NaCl and 5 MM $MgCl_2$ has been found to be suitable. After a certain time has passed, which essentially depends on the amount of the enzyme to be determined, an aliquot is applied to a silica gel plate. The dipeptide of the formula I (n=1) is applied as the reference substance for the reaction product. After chromatographic separation in a suitable system, such as, for example, n-butanol/glacial acetic acid/n-heptane, preferably in the ratio 10:8:7 by volume, the amount of the reaction product formed can be quantitatively determined. The evaluation can be visual or, strictly quantitative, by the densitometric methods which are well-known to those skilled in the art.

In this manner, the tripeptide according to the invention can also be employed to determine DD-carboxypeptidase in culture broths of streptomycetes such as, for example, streptomyces R 39, for the purification of this enzyme and for the determination of DD-carboxypeptidase inhibitors. A known excess of DD-carboxypeptidase is added to a sample containing DD-carboxypeptidase inhibitors. The amount of inhibitors can then be found from the difference between the DD-carboxypeptidase added and its remaining activity.

Determination of the DD-carboxypeptidase activity in the determination of β-lactams also takes place directly, i.e. without a coupled test mixture, since again in this instance the substrate according to the invention and the dipeptide produced therefrom are identified after chromatographic separation by the inherent color or fluorescence typical of the chromophore.

However, a particular advantage of the present invention is that, for the determination of the DD-carboxypeptidase activity remaining after pre-treatment with solutions containing β-lactams, it is not necessary to use elaborate apparatus, such as, for example HPLC, to separate the substrate according to the invention and the chromophore-containing dipeptide which has, where appropriate, been produced by the action of DD-carboxypeptidase. On the contrary, the separation is achieved merely on simple thin-layer plates, such as, for example, silica gel F 254 (Merck) with a suitable mobile phase, preferably n-butanol/glacial acetic acid/n-heptane (10:8:7). For a semi-quantitative assessment of the remaining DD-carboxypeptidase activity, it suffices to assess visually the intensity of the intense yellow spot due to the substrate or reaction product according to the invention or of the green fluorescence of these compounds visible on the chromatogram under long-wavelength ultraviolet light.

It is an additional advantage that the use of the substrate according to the invention makes it unnecessary to determine one of the two reaction products (D-alanine) using a multiply coupled test mixture. This is particularly valuable for an important area of use of this test, the determination of β-lactams in culture broths of microorganisms, since experience has shown that systems of this type frequently interfere with the coupled test mixture in such a manner that a determination of the D-alanine formed enzymatically becomes impossible. For this reason, the use of the tripeptide according to the invention for determining β-lactams in complex biological systems, in particular in fermentation broths of microorganisms, is particularly valuable.

A further advantage of the determination procedure according to the invention can be regarded as being the fact that a large number of tests can be carried out in a simple manner in parallel and simultaneously evaluated on a single thin-layer plate of appropriate dimensions.

EXAMPLE 1

Ac-Lys(NBF)-D-Ala-D-Ala-OH (a) Ac-Lys(NBF)-OH

A suspension of 1.08 g of 7-chloro-4-nitrobenzofurazan (5.4 mmole) in 250 ml of methanol is added, at room temperature, to a solution of 0.77 g of N-acetyl-L-lysine (4.1 mmole) in 200 ml of 0.6 N $NaHCO_3$. The mixture is stirred at room temperature overnight. Next day, methanol is removed in a rotary evaporator at 40° C. and the aqueous phase is extracted several times with ethyl acetate. The aqueous phase is acidified to pH 2 with 6 N hydrochloric acid, extracted several times with ethyl acetate, the ethyl acetate phase thus obtained is dried over sodium sulfate and evaporated. The pure substance is isolated by chromatography on silica gel in ethyl acetate/isopropanol/water (4:3:2).

Yield 960 mg. Melting point 119°–122° C.
$[\alpha]_D^{23} = -56.6°$ (c=1, 50% acetic acid).

(b) H-D-Ala-D-Ala-OBu$^t$. HCl 2.6 ml of N-ethylmorpholine and 4.4 g of DCC are added, at 0° C., to a solution of 4.46 g (20 mmole) of Z-D-Ala-OH, 3.87 g of H-D-Ala-OBu$^t$. HCl and 2.7 g of HOBt in 50 ml of dimethylformamide. The mixture is stirred at 0° C. for two hours and allowed to stand at room temperature overnight. Next day, the precipitate is filtered off with suction and the filtrate is evaporated under high vacuum. The residue is distributed between water and ethyl acetate. The ethyl acetate phase is extracted by shaking with a $KHSO_4/K_2SO_4$ buffer and then with saturated $NaHCO_3$ solution and water, dried over sodium sulfate and evaporated.

Yield: 8.7 g.

For purification, the substance is chromatographed on 800 g of silica gel in methylene chloride/acetone (0.5:0.5).

Yield 6.7 g of an oily substance.

The 6.7 g of Z-D-Ala-D-Ala-OBu$^t$ obtained above are dissolved in 300 ml of methanol and, after addition of Pd/carbon catalyst, are catalytically hydrogenated in an autotitrator with the addition of about 1 N methanolic HCl. After hydrogenation is complete, the catalyst is filtered off with suction and the filtrate is evaporated and dried under high vacuum. 4.1 g of amorphous hygroscopic substance, which is, however, homogeneous by TLC, remain.

$[\alpha]_D^{24} = +36.0°$ (c=0.5, methanol).

TLC: $R_f=0.65$ in n-butanol/glacial acetic acid/water (8:2:2).

(c) Ac-Lys(NBF)-D-Ala-D-Ala-OH 0.5 ml of N-ethylmorpholine and 880 mg of DCC are added, at 0° C., to a solution of 1.4 g of Ac-Lys(NBF)-OH, 1.08 g of H-D-Ala-D-Ala-OBu$^t$.HCl and 540 mg of HOBt in 10 ml of absolute tetrahydrofuran. The mixture is stirred at 0° C. for 2 hours and allowed to stand overnight at room temperature. Next day, the mixture is diluted with 100 ml of ethyl acetate and the precipitate is filtered off with suction. The filtrate is extracted by shaking with water, saturated $NaHCO_3$ solution, $KHSO_4/K_2SO_4$ buffer and again with saturated $NaHCO_3$ solution, dried over sodium sulfate and evaporated. The residue is vigorously stirred with about 20 ml of methylene chloride/methanol (19:1). During this, a substance crystallizes out and is filtered off with suction.

Yield 810 mg, melting point 120°–125° C.

The substance is homogeneous by TLC in methylene chloride/methanol (19:1). Ac-Lys(NBF)-D-Ala-D-Ala-OBu$^t$ is still present in the mother liquor. The pure substance is isolated by chromatography on silica gel in methylene chloride/methanol (19:1).

Yield 150 mg. Total yield of Ac-Lys(NBF)-D-Ala-D-Ala-OBu$^t$: 960 mg.

The 960 mg of Ac-Lys(NBF)-D-Ala-D-Ala-OBu$^t$ obtained above are dissolved in 20 ml of 90% strength trifluoroacetic acid. The mixture is allowed to stand at room temperature for one hour, evaporated and the residue is dissolved in water. Insolubles are filtered off with suction and the filtrate is freeze-dried.

Yield 530 mg, melting point 121° C. (partial sublimation), $[\alpha]_D^{27} = +20.8°$ (c=1, in 50% strength acetic acid).

The peptide is in the form of the monohydrate according to elementary analysis.

$C_{20}H_{27}N_7O_8 \cdot H_2O$ (511.5): Calculated: C 46.95, H 5.71, N 19.17. Found: C 46.3, H 5.7, N 18.6.

EXAMPLE 2

Ac-Lys(NBF)-D-Ala-D-Ala-OH . CH$_3$COOH (a) H-D-Ala-D-Ala-OH 5.4 g of H-D-Ala-D-Ala-OBu$^t$.HCl are dissolved in 25 ml of semi-concentrated hydrochloric acid and immediately evaporated under high vacuum. The residue is dissolved in a little methanol and the acid solution is immediately neutralized with N-ethylmorpholine. The dipeptide can be precipitated by the addition of methylene chloride. The precipitate is allowed to stand at 0° C. for four hours, filtered off with suction and washed with methylene chloride.

Yield 2.15 g, melting point 246°–248° C.
$[\alpha]_D^{28} + 17.6°$ (c=1, water).

(b) Ac-Lys(NBF)-D-Ala-D-Ala-OH.CH$_3$COOH 210 mg of DCC are added, at 0° C., to a solution of 351 mg of Ac-Lys(NBF)-OH and 163 mg of HOOBt in 3 ml of absolute tetrahydrofuran, the mixture is stirred at 0° C. for two hours and at room temperature for one hour and then 160 mg of H-D-Ala-D-Ala-OH and 3 ml of dimethylformamide are added. The mixture is stirred at room temperature for a further 4 hours and allowed to stand overnight at room temperature. Next day, the mixture is evaporated and the residue is triturated with hot water. Insolubles are filtered off with suction and the filtrate is evaporated. The residue is chromatographed on silica gel in n-butanol/glacial acetic acid/n-heptane (10:5:5). The fractions which contain pure Ac-Lys(NBF)-D-Ala-D-Ala-OH are combined and evaporated. The residue is dissolved in water and freeze-dried.

Yield 180 mg, melting point 164° C.

According to TLC in n-butanol/glacial acetic acid/n-heptane (10:5:5), the derivative is homogeneous and identical to that prepared according to Example 1. Two acetyl groups are seen in the NMR spectrum, and these indicate that the peptide is in the form of the acetate.

Another indication that the substance is in the form of the acetate is the fact that the peptide prepared according to Example 1 had a melting point of 165° C. after it had been dissolved in acetic acid and freeze-dried again.

EXAMPLE 3

Ac-Lys(NBF)-D-Ala-OH (for chromatographic comparison)

0.26 ml of dimethylformamide and 440 mg of DCC are added, at 0° C., to a solution of 702 mg of Ac-Lys(NBF)-OH, 400 mg of H-D-Ala-OBu$^t$.HCl and 270 mg of HOBt in 6 ml of dimethylformamide. The mixture is stirred at 0° C. for two hours and allowed to stand overnight at room temperature. Next day, the mixture is diluted with 50 ml of ethyl acetate, and extracted by shaking with water, saturated NaHCO$_3$ solution, KHSO$_4$/K$_2$SO$_4$ buffer and saturated NaHCO$_3$ solution. The ethyl acetate phase is dried over Na$_2$SO$_4$ and evaporated. The residue is chromatographed on silica gel in methylene chloride/methanol (20:1).

Yield 400 mg.

The 400 mg of Ac-Lys(NBF)-D-Ala-OBu$^t$ obtained are dissolved in 10 ml of 90% strength trifluoroacetic acid. The mixture is allowed to stand at room temperature for one hour and evaporated. The residue is dissolved in water and freeze-dried.

Yield 300 mg, melting point 112° C., $[\alpha]_D^{32} = +0.9°$ (c=1, 50% strength acetic acid).

The peptide is in the form of the monohydrate according to elementary analysis.

$C_{17}H_{22}N_6O_7 \cdot H_2O$ (440.4): Calculated: C 46.3, H 5.49, N 19.08. Found: C 45.6, H 5.2, N 18.6.

We claim:

1. A chromophoric peptide of the formula I

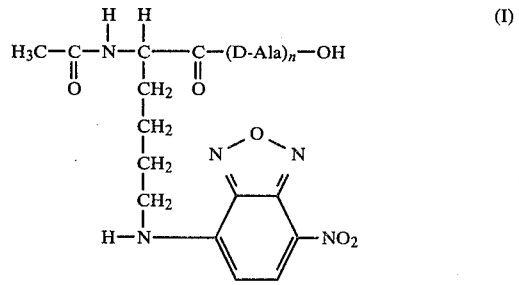

in which n represents 1 or 2.

* * * * *